United States Patent
Yamasaki et al.

(10) Patent No.: US 7,592,311 B2
(45) Date of Patent: Sep. 22, 2009

(54) PLATELET PRODUCTION PROMOTING AGENT

(75) Inventors: Motoo Yamasaki, Tokyo (JP); Masami Okabe, Shizuoka (JP); Toshiyuki Suzawa, Kanagawa (JP); Ken Kobayashi, Tokyo (JP); Kumiko Maruyama, Shizuoka (JP)

(73) Assignee: Kyowa Hakko Kirin Co., Ltd., Tokyo (JP)

( * ) Notice: Subject to any disclaimer, the term of this patent is extended or adjusted under 35 U.S.C. 154(b) by 841 days.

(21) Appl. No.: 11/253,617

(22) Filed: Oct. 20, 2005

(65) Prior Publication Data

US 2006/0040865 A1 Feb. 23, 2006

Related U.S. Application Data

(62) Division of application No. 10/084,615, filed on Feb. 28, 2002, now abandoned, which is a division of application No. 08/696,988, filed as application No. PCT/JP95/00266 on Feb. 23, 1995, now Pat. No. 6,245,900.

(30) Foreign Application Priority Data

Feb. 23, 1994  (JP) ................................. P. 6-25735

(51) Int. Cl.
A61K 38/00 (2006.01)
A61K 38/17 (2006.01)
(52) U.S. Cl. ........................ 514/12; 530/350; 530/402; 530/351
(58) Field of Classification Search .................. None
See application file for complete search history.

(56) References Cited

U.S. PATENT DOCUMENTS

| | | | |
|---|---|---|---|
| 4,968,616 A | 11/1990 | Inoue et al. |
| 5,214,132 A | 5/1993 | Kuga et al. |
| 5,310,881 A | 5/1994 | Sakurai et al. |
| 5,342,940 A | 8/1994 | Ono et al. |
| 5,714,581 A | 2/1998 | Kuga et al. |
| 5,795,968 A | 8/1998 | Kuga et al. |
| 5,824,778 A | 10/1998 | Ishikawa et al. |

FOREIGN PATENT DOCUMENTS

| | | |
|---|---|---|
| EP | 0 098 110 A2 | 1/1984 |
| EP | 0 335 423 B1 | 10/1989 |
| EP | 0 401 384 | 12/1990 |
| EP | 0 473 268 A2 | 3/1992 |
| JP | A-59-59629 | 4/1984 |
| JP | 63-267292 | 12/1987 |
| JP | A-63-60938 | 3/1988 |
| JP | B-96558 | 12/1989 |
| JP | A-3-215499 | 9/1991 |
| JP | A-4-503821 | 7/1992 |
| WO | WO 91/07988 | 6/1991 |
| WO | WO 94/20069 | 9/1994 |

OTHER PUBLICATIONS

Ishikawa et al Gen. Pharmac. vol. 25, No. 3 pp. 333-537, 1994 "Pharmacological Effects of Recombinant Human Granulocyte Colony-Stimulating Factor Modified by Polyethylene Glycol on Anticancer Drug-Induced Neutropenia in Mice".
Inoue et al "Modification of Billirubin Oxidase . . . " Caplus #1989; 628013.
Maeda et al "Conjugation of PolyLstyrene-lo-maleic acid) Derivatives to the Antitumor protein NCS: . . . " J. Med. Chem. V. 28, pp. 455-461, 1985.
International Search Report dated Jun. 13, 1995 issued in PCT/JP95/00266 (3 pages).
Tanikawa et al, "Effects of Recombinant Granulocyte Colony-stimulating Factor (rG-CSF) and Recombinant Granulocyte-Macrophage Colony-stimulating Factor (rGM-CSF) on Acute Radiation Hematopoietic Injury in Mice", Exp. Hematol. 17:883-888 (1989).
Koike et al, AN 91:490291 Biosis (1991).
Avenarius et al, AN 92:505439 Biosis (1992).
Washizuka et al, AN 92:197606 Medline (1992).
Shimoda, K. et al, AN 93:214499 Biosis (1993).
Shimoda et al, AN 93:294721 Biosis (1993).
Koike et al, International Congress Series, 956, "Myelodysplastic Syndrome and Cytokines; International Symposium, Sapporo, Japan, Sep. 28-29, 1990", pp. 289-292 (1991), Elsevier Science Publishers B.V.
Washizuka et al, American Journal of Hematology 39:153-154 (1992).
Appendix A (blowback Fig. 1 of Washizuka et al in which arrows were added for emphases), American Journal of Hematology 39:153-154 (1992).

*Primary Examiner*—Michael Borin
(74) *Attorney, Agent, or Firm*—Nixon & Vanderhye P.C.

(57) ABSTRACT

The invention relates to a polypeptide wherein at least one of the amino, carboxyl, mercapto or guanidino group in a polypeptide molecule having human granulocyte colony stimulating factor activity is chemically modified by a chemical modifying agent, and a platelet production promoter comprising said polypeptide, a method for treating a patient with decreased platelet counts comprising administering an effective amount of said polypeptide to the patient, the use of said polypeptide for the production of pharmaceutical compositions which are useful for the treatment of the patient with decreased platelet counts, and the compositions for treating the patient with decreased platelet counts, which comprises an effective dose of said polypeptide in a pharmaceutically acceptable dosage form with a pharmaceutical acceptable carrier.

8 Claims, No Drawings

```
                        SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
        (A) LENGTH: 175 amino acids
        (B) TYPE: amino acid
        (C) STRANDEDNESS: <Unknown>
        (D) TOPOLOGY: linear (ii) MOLECULE TYPE: protein (xi) SEQUENCE DESCRIPTION: SEQ ID NO: 1:

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Gly Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

PLATELET PRODUCTION PROMOTING AGENT

The present application is a divisional of application Ser. No. 10/084,615, filed Feb. 28, 2002 now abandoned, which is a divisional of application Ser. No. 08/696,988, filed Aug. 16, 1996, now issued as U.S. Pat. No. 6,245,900 on Jun. 2, 2001, which is a 371 U.S. National Phase of PCT/JP95/00266, filed 23 Feb. 1995, which claims benefit of Hei 6-25735, filed 23 Feb. 1994, the entire contents of each of which is incorporated herein by reference.

INDUSTRIAL FIELD OF THE INVENTION

The invention relates to a chemically modified human granulocyte colony stimulating factor polypeptide which is produced by chemically modifying at least one of the amino, carboxyl, mercapto or guanidino group in a polypeptide molecule having human granulocyte colony stimulating factor (hereinafter referred to as hG-CSF) activity, and a platelet production promoting agent comprising said polypeptide, a method for treating a patient with decreased platelet counts comprising administering an effective amount of said polypeptide to the patient, the use of said polypeptide for the production of pharmaceutical compositions which are useful for the treatment of patients with decreased platelet counts, and compositions for treating patients with decreased platelet counts, which comprise an effective amount of said polypeptide in a pharmaceutically acceptable dosage form together with a pharmaceutically acceptable carrier.

BACKGROUND ART

Interleukin 6 [F. Takatsuki et al., Cancer Research, 50, 2885-2890 (1990)], leukemia inhibitory factor [D. Metcalf et al. Blood, 76, 50-56 (1990)], stem cell factor [P. Hunt et al. Blood, 80, 904-911 (1992)], macrophage colony stimulating factor (M-CSF; Japanese Published Examines Patent Application No. 11705/94) and thrombopoietin [de Sauvage et al. Nature, 369, 533 (1994)] are known as substances which possibly promote platelet production. Furthermore, conagenin [Japanese Cancer Association #2235 (1992)], Y25510 [The 113rd annual meeting of Pharmaceutical Society of Japan, PB13-22 (1993)], 2-pyranone derivatives [Japanese Published Unexamined Patent Application No. 213758/93], and FK565 (WO93/23066) are known as low molecular weight substances which possibly promote platelet production.

It is known that hG-CSF is one of the polypeptides essential for hemopoietic stem cell growth and differentiation leading to the formation of various types of hemocytes, and exerts growth-promoting effect on most granulocytes and in particular neutrophils.

As a modified polypeptide exhibiting hG-CSF activity wherein groups are chemically modified with a chemical modifying agent, a chemically modified hG-CSF obtained by modifying at least one amino group of the polypeptide exhibiting hG-CSF activity with a polyethylene glycol derivative is known (Japanese Published Unexamined Patent Application No. 316400/89, WO90/06952, Japanese Published Unexamined Patent Application No. 32559/92). It has not been known that these chemically modified hG-CSF polypeptides exert a platelet production promoting effect.

DISCLOSURE OF INVENTION

The invention relates to a chemically modified polypeptide wherein at least one of the amino, carboxyl, mercapto or guanidine group in the polypeptide molecule having hG-CSF activity is modified chemically, and a platelet production promoting agent comprising said polypeptide, a method for treating a patient with decreased platelet counts comprising administering an effective amount of said polypeptide to the patent, the use of said polypeptide for the production of pharmaceutical compositions which are useful for the treatment of patients with decreased platelet counts, and compositions for treating a patient with decreased platelet counts, which comprise an effective amount of said polypeptide in a pharmaceutically acceptable dosage form together with a pharmaceutically acceptable carrier.

More specifically, the invention relates to a chemically modified polypeptide wherein at least one of the amino, carboxyl, mercapto or guanidino group in the polypeptide molecule having hG-CSF activity is modified chemically with a polyalkylene glycol derivative or a styrene-maleic acid copolymer, and a platelet production promoting agent comprising said polypeptide, a method for treating a patient with decreased platelet counts comprising administering an effective amount of said polypeptide to the patient, the use of said polypeptide for production of pharmaceutical compositions which are useful for the treatment of patients with decreased platelet counts, and compositions for treating a patient with decreased platelet counts, which comprises an effective amount of said polypeptide in a pharmaceutically acceptable dosage form together with a pharmaceutically acceptable carrier.

The polyalkylene glycol derivatives include, for example, polyethylene glycol derivatives, polypropylene derivatives, and polyethylene-polypropylene copolymer derivatives.

With more specific reference to the agents for chemically modifying at least one of amino, carboxyl, mercapto and guanidino groups, the amino group-chemical modifying agent includes, for example, polyalkylene glycol derivatives having the formula (I):

$$R^1\text{-}(M)_n\text{-}X\text{—}R^2 \qquad (I)$$

wherein $R^1$ represents an alkyl or alkanoyl group; M represents the formula:

$$\text{—OCH}_2\text{CH}_2\text{—}, \text{—OCH}_2\text{CH}_2\text{CH}_2\text{—},$$

or $$\text{—(OCH}_2\text{CH}_2)_r\text{—(OCH}_2\text{CH}_2)_s\text{—}$$

wherein r and s have any variable positive integral values, which are the same or different; n has any variable positive integral values; X represents a single bond, O, NH, or S; and $R^2$ represents the formula:

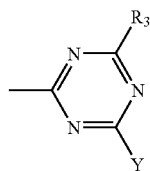

wherein $R^3$ represents OH, halogen, or the formula:

$$\text{—}X^a\text{-}(M^a)_{na}\text{-}R^{1a}$$

wherein $X^a$, $M^a$, $R^{1a}$ and na have the same meanings as the above-mentioned X, M, $R^1$ and n, respectively, and Y represents halogen or the formula:

$$\text{-Z-(CH}_2)_p\text{—(O)}_m\text{—W}$$

wherein Z represents O, S, or NH; W represents a carboxyl group, an active derivative thereof, or the formula:

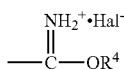

wherein $R^4$ represents an alkyl group; and Hal represents halogen, and p has an integral value of 1 to 6; and m has a value of 0 or 1,

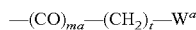

wherein $W^a$ and ma have the name meanings as the above-mentioned W and m, respectively; and t has an integral value of 0 to 6, or

wherein $Hal^a$, pa and $R^{4a}$ have the same meanings as the above-mentioned Hal, p and $R^4$, respectively, and styrene-maleic acid copolymers having the formula (II):

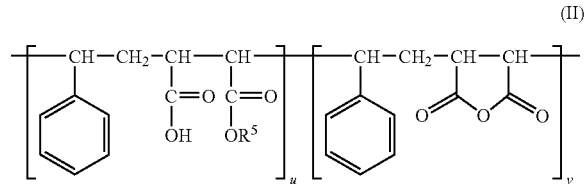

(II)

wherein u and v have any variable positive integral values, which are the same or different; and $R^5$ represents a hydrogen atom, or an alkyl group. The carboxyl group-chemical modifying agents include, for example, polyalkylene glycol derivatives having the formula (III):

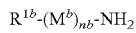

(III)

wherein $M^b$, $R^{1b}$ and nb have the same meanings as the above-mentioned M, $R^1$ and n, respectively. The mercapto group-chemical modifying agent are polyalkylene glycol derivatives having the formula (IV):

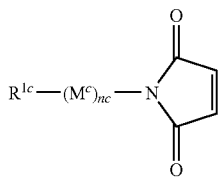

(IV)

wherein $M^c$, $R^{1c}$, and nc have the same meanings as the above-identified M, $R^1$, and n, respectively, and styrene-maleic acid copolymers having the formula (V):

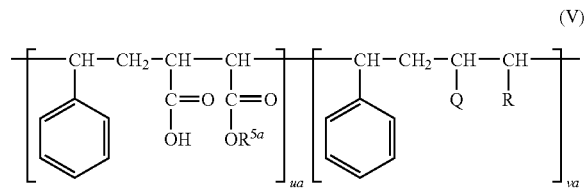

(V)

wherein $R^{5a}$, ua, and va have the same meanings as the above-identified $R^5$, U, and V, respectively, and one of Q and R represents a carboxyl group, and the other represents the formula:

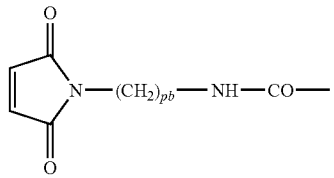

wherein pb has the same meanings as the above-identified p. The guanidino group-chemical modifying agent includes, for example, polyalkylene glycol derivatives having the formula (VI):

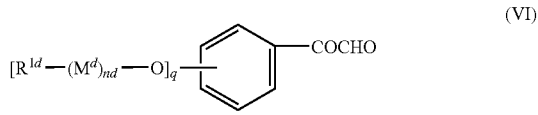

(VI)

wherein q has a value of 1, or 2, and $M^d$, $R^{1d}$, and nd have the same meanings as the above-identified M, $R^1$, and n, respectively.

In the chemical modifying group as used in the present invention, the alkyl group represented by $R^1$, $R^4$, and $R^5$ includes, for example, linear or branched groups having from 1 to 18 carbon atoms such as methyl, ethyl, propyl, isopropyl, butyl, isobutyl, sec-butyl, tert-butyl, pentyl, isopentyl, hexyl, isohexyl, heptyl, octyl, isooctyl, decyl, dodecyl, tetradecyl, hexadecyl, and octadecyl; the alkanoyl groups represented by $R^1$ include, for example, linear or branched groups having from 1 to 18 carbon atoms such as formyl, acetyl, propionyl, butyryl, valeryl, pivaroyl, pentanoyl, lauroyl, myristoyl, palmitoyl, and stearoyl; the halogen represented by $R^3$, Y, and Hal includes, for example, chlorine, bromine, and iodine atoms; the active derivatives of a carboxyl group represented by W includes, for example, acid halides such as acid chloride and acid bromide, active esters such as p-nitrophenyl ester and N-oxysuccinimide, and mixed anhydrides including monoethylester carbonate and monoisobutyl carbonate. The symbols n, r, s, u, and v stand for positive integral values of 1 to 1,000, and preferably, n is 7 to 500, and r, s, u and v are each between 1 and 200. The molecular weights of chemically modifying groups range from 500 to 100,000, and preferably range from 1,000 to 40,000.

As the polypeptides having hG-CSF activity of the present invention, any peptide having hG-CSF activity can be used, and preferably, polypeptides comprising the amino acid sequence of SEQ ID NO:1, a part of said sequence, or the amino acid sequence, in which a part of amino acids of said sequence are substituted by other amino acids [Nature, 319, 415 (1986), Japanese Published Unexamined Patent Application No. 267292/88, Japanese Published Unexamined Patent Application No. 299/88, and WO87/01132], can be used. An embodiment of polypeptides comprising the amino acid sequence in which a part of the sequence is substituted by other amino acids (hG-CSF derivatives) is illustrated in Table 1.

TABLE 1

| Position from N-terminal amino acid | Substituted amino acid in hG-CSF derivatives | | | | | | | | | | | |
|---|---|---|---|---|---|---|---|---|---|---|---|---|
| (hG-CSF of SEQ ID NO:1) | a) | b) | c) | d) | e) | f) | g) | h) | i) | j) | k) | l) |
| 1st (Thr) | * | Val | Cys | Tyr | Arg | * | Asn | Ile | Ser | * | Ala | * |
| 3rd (Leu) | Glu | Ile | Ile | Ile | Thr | Thr | Glu | Thr | Thr | * | Thr | * |
| 4th (Gly) | Lys | Arg | Arg | Arg | Arg | Arg | Arg | Arg | Arg | Arg | Tyr | * |
| 5th (Pro) | Ser | Ser | Ser | Ser | Ser | Ser | Ser | Ser | Ser | * | Arg | * |
| 17th (Cys) | Ser | Ser | Ser | Ser | Ser | Ser | Ser | Ser | Ser | Ser | Ser | Ser |

*unsubstituted amino acid

In the molecule of the peptides having hG-CSF activity in which more than one group is generally present with respect of each of amino, carboxyl, mercapto, and guanidino groups, one of these groups is enough to be chemically modified.

The peptides having hG-CSF activity can be chemically modified by the reaction of the chemical agents including polyalkylene glycol derivatives such as polyethylene glycol derivatives, polypropylene glycol derivatives and polyethylene glycol-polypropylene glycol copolymer derivatives, and styrene-maleic acid copolymer derivatives with the polypeptide (hG-CSF derivatives) comprising amino, carboxyl, mercapto, or guanidino groups.

As the method for the reaction of the polypeptide comprising amino, carboxyl, mercapto, or guanidino groups with polyethylene glycol derivatives or polypropylene glycol derivatives, the conventional methods [e.g., Japanese Published Unexamined Patent Application No. 316400/89, Biotech. Lett., 14, 559-564 (1992), BIO/TECHNOLOGY, 8, 343-346 (1990)] or their modifications can be used.

As the method for the reaction with polyethylene glycol-polypropylene glycol copolymer derivatives, the conventional methods [e.g., Japanese Published Unexamined Patent Application No. 59629/84, Japanese Published Unexamined Patent Application No. 176586/85, WO89/06546, EP0539167A2] or their modifications can be used.

As the method for the reaction with styrene-maleic acid copolymer derivatives, the conventional methods [e.g., BIO INDUSTRY 5, 499-505 (1988), Japanese Published Unexamined Patent Application No. 85922/89, Japanese Published Unexamined Patent Application No. 99573/89] or their modifications can be used.

As an example of the chemically modified peptide with hG-CSF activity, modified peptides obtained by binding at least one amino group of hG-CSF with a group described by the following formula (Ia):

$$R^1-(OCH_2CH_2)_n-X-R^{2a}- \quad (Ia)$$

wherein $R^1$ represents an alkyl or alkanoyl group; n has any variable positive integral value; X represents a single bound, O, NH, or S; and $R^{2a}$ represent the formula:

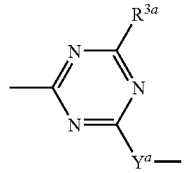

wherein $R^{3a}$ represents OH, halogen, or the formula:

wherein $X^a$, $R^{1a}$ and na are identical to said X, $R^1$ and n, respectively, and $Y^a$ represents a single bond or the formula:

$$-Z-(CH_2)_p-(O)_m-CO-$$

wherein Z represents O, S, or NH; p has an integral value of 1 to 6; and m has a value of 0 or 1, $$-(CO)_{na}-(CH_2)_t-CO-$$

wherein ma is identical to said m; and t has an integral value of 0 to 6.

In each group of the formula (Ia), the alkyl group, alkanoyl group, halogen, and positive integral value are defined similarly to those in said formula (I).

In addition, a novel chemically modified hG-CSF or chemically modified hG-CSF derivative can be provided by the present invention.

As the novel chemically modified hG-CSF, modified peptides obtained by binding at least one amino group and a group described by the following formula (Ib):

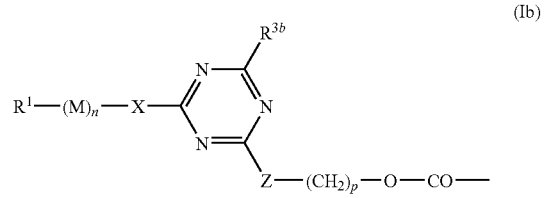

wherein $R^1$ represents an alkyl or alkanoyl group; M represents the formula:

$$-OCH_2CH_2-, -OCH_2CH_2CH_2-$$

or $$-(OCH_2CH_2)_r-(OCH_2CH_2CH_2)_s-$$

wherein r and s have any variable positive integral values, which are the same or different, n has any variable positive integral value; X represents a single bond, O, NH, or S; $R^{3b}$ is identical to $R^{3a}$; Z represents O, S, or NH; and p has an integral value of from 1 to 6.

From 1 to 5 molecules of polyethylene glycol derivatives, polypropylene glycol derivatives, polyethylene glycol-polypropylene glycol copolymer derivatives or styrene-maleic acid copolymer derivatives bind to chemically modified hG-CSF or chemically modified hG-CSF derivatives. Consequently, the chemically modified hG-CSF and chemically modified hG-CSF derivatives are used in the from of a mixture of 1 to 5 molecular combinations, or each fractionated combination. In the fractionation of the chemically modified hG-CSF and chemically modified hG-CSF derivatives, various chromatographies such as ion-exchange chromatography, gel filtration chromatography, reversed-phase chromatography, and hydrophobic chromatography, and ammonium sulfate fractionation can be applied, which are usually used in the fractionation of long-chain polypeptides and the like.

The degree of chemical modification is confirmed by the reduction in free groups, which is determined by monitoring the morbidity of chemically modified hG-CSF using sodium dodecyl sulfate polyacrylamide gel electrophoresis.

The protein assay in the invention was performed by the following experimental methods.

Experimental Method 1

In the present invention, the protein concentration was determined by the method of Lowry et al. [Lowry, O. H. et al., J. Biol. Chem., 193, 265 (1951)].

Experimental Method 2

According to the method of Laemmli [U. K. Laemmli: Nature, 227, 680 (1970)], SDS-polyacrylamide gel electrophoresis was performed, and after staining proteins separated on said gel with Coomassie brilliant blue, the protein concentration was determined using a chromatoscanner (CS-930, Shimadzu Corporation).

The following experimental examples serve to illustrate the pharmacological activity of the chemically modified hG-CSF and chemically modified hG-CSF derivatives.

Experimental Example 1

G-CSF activity and promoting effect on leukemic cells, NFS-60 cells of the chemically modified hG-CSF and chemically modified hG-CSF derivatives.

The activity of the chemically modified hG-CSF and chemically modified hG-CSF derivatives obtained in following Reference examples 4, 6, 8, 12, 15, 17, 19, 20 and Example 4 to mouse bone marrow cells were determined according to the method of Okabe et al. [M. Okabe et al., Blood, 75, 1788 (1990)]. Furthermore, the growth promoting activity against the NSF-60 cells [K. Holmes et al. Proc. Natl. Acad. Sci. USA, 82, 6687 (1985)] according to the method of Asano et al. [Asano et al. Jpn. Pharmacol. Ther. 19, 2767 (1991)]. The results are illustrated in Table 2.

Experimental Example 2

Promoting effect on the recovery of reduced platelets in total-body irradiated mice In the studies illustrated in Tables 3 and 4, 5 male BALB/c mice (10 weeks of age) were used, and in the study illustrated in Table 5, 4 male BALB/c mice (6 weeks of age) were used. After 3 Gy of total-body irradiation (hereinafter referred to as Rx) per mouse from $^{137}$Cs radioactive source (RI-433, Toshiba Corporation), these mice were raised in a cleaned cage in a specific pathogen-free environmental site. Water and feed were available ad libitum. As untreated controls, mice without irradiation were similarly raised.

The chemically modified hG-CSF and chemically modified hG-CSF derivatives illustrated in Tables 3 to 5 were dissolved into physiological saline respectively, and administered subcutaneously at a single dose of 5 μg/0.2 ml per mouse, wherein the solution of a chemically modified hG-CSF derivative (tri-type) was administered once on the day after Rx, or twice on the day after Rx and on the 5th day in the study illustrated in Table 3, and the chemically modified hG-CSF and chemically modified hG-CSF derivatives were administered once on the day after Rx in the studies illustrated in Table 4 and 5.

Blood was sequentially collected from the murine vein of eyeground, and the platelet count was determined using an automatic cell counter (CC-180A, TOA MEDICAL ELECTRONICS CO., Ltd.). The results are shown in Tables 3 to 5.

TABLE 3

| Administration of chemically modified | Mean platelet count (%)[*2] days after start of irradiation | | | | | |
|---|---|---|---|---|---|---|
| hG-CSF derivatives[*1] | 0 | 5 | 9 | 11 | 13 | 20 |
| Untreated | 100 | 95.7 | 37.7 | 53.5 | 59.5 | 80.6 |
| Administered on 1st day | 100 | 94.5 | 54.0 | 109.8 | 100.3 | 94.8 |
| Administered on 1st and 5th day | 100 | 100.1 | 40.2 | 118.6 | 101.3 | 105.1 |

[*1]Chemically modified hG-CSF derivative (tri-type) of Reference example 4.
[*2]Relative mean platelet count (%) when the count of non-irradiated control group is 100.

TABLE 2

| HG-CSF[*1] (Derivatives) | Chemically modified compounds | Number of the modified compound molecules binding to one hG-CSF molecule | Production promoting activity (%)[*2] | |
|---|---|---|---|---|
| | | | Bone marrow cells | NFS60 cells |
| Reference example 3 | None | 0 | 100 | 100 |
| Reference example 3 | Reference example 4 | 3 | 18 | 21 |
| Reference example 3 | Reference example 6 | 1-4 | | 15 |
| SEQ ID NO: 1 | Reference example 8 | 1-4 | | 19 |
| Reference example 3 | Reference example 9 | 1-4 | | 12 |
| SEQ ID NO: 1 | Reference example 11 | 1-3 | | 17 |
| Reference example 3 | Reference example 12 | 1-3 | | 33 |
| Reference example 3 | Reference example 15 | 1-4 | | 11 |
| Reference example 3 | Reference example 17 | 3 | | 24 |
| Reference example 3 | Reference example 17 | 2 | | 40 |
| Reference example 3 | Reference example 17 | 1 | | 61 |
| Reference example 3 | Example 4 | 3 | | 17 |
| Reference example 3 | Example 4 | 2 | | 24 |
| Reference example 3 | Example 4 | 1 | | 53 |

[*1]Origin of used hG-CSF or hG-CSF derivatives.
[*2]Relative activity (%) when the activity of hG-CSF derivative produced in the Reference example is 100%.

TABLE 4

| Administered chemically modified | Mean platelet count (%)* days after start of irradiation | | | | | | |
|---|---|---|---|---|---|---|---|
| hG-CSF (derivatives) | 0 | 6 | 8 | 9 | 10 | 11 | 12 |
| Untreated | 100 | 88.9 | 36.2 | 42.1 | 51.2 | 67.6 | 74.2 |
| Reference example 8 | 100 | 101 | 41.1 | 63.2 | 98.5 | 126 | 133 |
| Reference example 9 | 100 | 103 | 41.0 | 66.3 | 98.9 | 142 | 159 |
| Reference example 11 | 100 | 84.1 | 34.5 | 51.6 | 81.3 | 112 | 130 |
| Reference example 12 | 100 | 93.1 | 42.4 | 66.1 | 92.7 | 145 | 140 |

*Relative mean platelet count (%) when the count of non-irradiated control group is 100.

TABLE 5

| Administered chemically modified | Mean platelet count (%)* days after start of irradiation | | | | | |
|---|---|---|---|---|---|---|
| hG-CSF (derivatives) | 0 | 6 | 8 | 10 | 11 | 12 |
| Untreated | 100 | 58.9 | 26.6 | 35.1 | 38.3 | 45.1 |
| Reference example 19 | 100 | 55.1 | 30.5 | 62.7 | 98.5 | 103.6 |
| Reference example 20 | 100 | 52.4 | 29.1 | 61.3 | 84.6 | 105.1 |

*Relative mean platelet count (%) when the count of non-irradiated control group is 100.

In the mice receiving 3 Gy of total-body irradiation group, the platelet count markedly decreased, reached the minimum at the 8th to 9th day of Rx, and subsequently increased gradually; however, throughout the studies, the platelet count did not recover to the pre-irradiation level. However, in the mice receiving the chemically modified hG-CSF and chemically modified hG-CSF derivatives, reduction of platelet count was suppressed, the count markedly increased at the 8th to 9th day after irradiation, and the count completely recovered to its pre-irradiation level at the 11th to 12th day after irradiation. A similar effect was also seen in the group in which the agents were administered on the day after Rx and on the 5th day.

Experimental Example 3

Promoting effect on the recovery against reduced platelet under anti-cancer drug treatment 5-Fluorouracil (5-FU, Kyowa Hakko Kogyo Co., Ltd.), an anti-tumor agent, was administered intraperioneally to 5 male BALB/C mice (9 weeks of age) at a dose of 100 mg/kg. On the day after 5-FU administration, the chemically modified hG-CSF (tri-type) obtained in Reference example 4 was dissolved into physiological saline, and administered subcutaneously in a single dose of 5 µg/0.2 ml per mouse. Blood was sequentially collected from the murine vein of eyeground, and the platelet counts were determined using an automatic cell counter. The results are shown in Table 6.

TABLE 6

| Administered chemically modified hG-CSF | Mean platelet count (%)*[2] days after start of administration of 5-FU | | | | |
|---|---|---|---|---|---|
| (derivatives)*[1] | 0 | 4 | 5 | 6 | 7 |
| Untreated | 100 | 31.2 | 27.1 | 39.1 | 60.4 |
| Administered at 1st day | 100 | 42.3 | 43.6 | 68.3 | 103.7 |

*[1]Chemically modified hG-CSF derivative (tri-type) of Reference example 4.
*[2]Relative mean platelet count (%) when the count of non-irradiated control group is 100.

In the 5-FU administration group, the platelet count decreased from the 4th day of administration, reached the minimum at the 5th day, and then recovered to its pre-administration level at the 9th day. In the chemically modified hG-CSF group, platelet reduction was suppressed, and a clear promoting effect on the recovery was noted after the 6th day. On Day 7 after administration, the platelet count recovered to its pre-administration level.

Experimental Example 4

Promoting effect on the recovery against reduced platelet in bone marrow transplantation After 10 Gy of Rx from $^{137}$Cs radioactive source (RI-433, Toshiba Corporation), 4 male BALB/c mice (8 weeks of age) were raised in a cleaned cage in a SPF environmental site. On the day after the irradiation, they were transplanted with $2\times10^6$ bone marrow cells (without adherent nylon wool) of the same strain. After 2 hours, the chemically modified hG-CSF (tri-type) obtained in Reference example 4 was dissolved into physiological saline, and administered subcutaneously at a single dose of 10 µg/0.2 ml, 20 µg/0.2 ml, or 40 µg/0.2 ml per mouse. Blood was sequentially collected from the murine vein at the eyeground and the platelet counts were determined using an automatic cell counter. The results are shown in Table 7.

TABLE 7

| Bone marrow transplantation | Dose of chemically modified hG-CSF derivatives*[1] (µg) | Mean platelet count (%)*[2] days after start of irradiation | | | | | |
|---|---|---|---|---|---|---|---|
| | | 0 | 7 | 11 | 12 | 13 | 15 |
| Untreated | 0 | 100 | 7.1 | 11.3 | 3.2 | 7.1 | dead |
| Transplanted | 0 | 100 | 6.3 | 15.8 | 29.1 | 52.3 | 75.8 |
| Transplanted | 40 | 100 | 6.6 | 21.4 | 42.0 | 81.5 | 118.7 |
| Transplanted | 20 | 100 | 6.9 | 23.9 | 46.6 | 86.1 | 117.6 |
| Transplanted | 10 | 100 | 7.9 | 17.6 | 43.8 | 79.8 | 108.7 |

*[1]Chemically modified hG-CSF derivatives (tri-type) of Reference example 4.
*[2]Relative mean platelet count (%) when the count of non-irradiated control group is 100.

All of the mice receiving 10 Gy of total-body irradiation experienced seriously reduced platelet counts, and died within 2 weeks. The mice with transplanted bone marrow cells did not die, but decrease of platelet count continued for more than 2 weeks. The bone marrow-transplanted mice receiving chemically modified hG-CSF showed the promoting effect on the recovery of platelet counts in a dose-dependent manner after the 11th day, and recover to more than its pre-irradiation level at the 15th day after irradiation.

Experimental Example 5 Acute Toxicity Test 4 male BALB/c mice at 5 to 10 weeks of age were received the chemically modified hG-CSF (tri-type) obtained in Reference example 4 at a single dose of 25 µg per mouse. In another test, after administration at a dose of 20 µg, further each 20 µg was administered at the 1st, 5th and 9th day after administration. In both tests, the mortality was observed to find that the mice underwent no change in the healthy condition and that no mice died.

As described in the experimental examples, the chemically modified hG-CSF and chemically modified hG-CSF derivatives show a clear promoting effect toward the recovery of platelet counts from seriously reduced platelet counts caused by irradiation, chemotherapy for cancer, or bone marrow transplantation, thus indicating its usefulness as a platelet production promoter.

In addition to the chemically modified hG-CSF and chemically modified hG-CSF derivatives, other cytokines or low-molecular platelet production promoters may be used. As the other cytokines, there are interleukin 3, interleukin 6, leukemia inhibitory factor, stem cell factor, macrophage colony stimulating factor, thrombopoietin, and the like. As low-molecular platelet production promoter, there are conagenin, Y25510, 2-pyranone derivatives, FK565, and the like.

The chemically modified hG-CSF and chemically modified hG-CSF derivatives can be used by themselves or in various dosage forms. The pharmaceutical compositions of the present invention can be produced by uniformly mixing an effective dose as an active component of the chemically modified hG-CSF and chemically modified hG-CSF derivatives and a pharmacologically acceptable carrier. Preferably, these pharmaceutical compositions are in a dosage form suitable for administration through injection.

Injectable preparations can be prepared using the chemically modified hG-CSF or chemically modified hG-CSF derivatives, and carriers such as distilled water, a salt solution, a glucose solution, or a mixture of a salt solution and a glucose solution. In this preparation, according to a conventional method, the preparations can be prepared in the form of a solution, suspension or dispersion, using a suitable auxiliary agent. Furthermore, lyophilized preparations can be prepared by lyophilizing said preparations. While the condition of lyophilization is not specifically restricted, usually, said preparations are frozen at less than −50° C. for 1 to 5 hours, dried at a shelf temperature of from −20° C. to 0° C., and at a vacuum of 50 to 150 mTorr for 24 to 48 hours, and subsequently at a shelf temperature of 10° C. to 30° C., and at a vacuum of 50 to 100 mTorr for 16 to 24 hours to obtain the lyophilized preparation.

The platelet production promoter of the invention can include various common pharmaceutical carriers, remedium constituents, diluents, stabilizers, or adsorption inhibitors.

While the dose and administration frequency are decided depending to the dosage form, the patient's age, body weight, subjective disease and conditions, usually, in an adult, 15 µg to 1.5 mg, preferably 25 to 500 µg of the chemically modified hG-CSF or chemically modified hG-CSF derivatives are administered 1 to 7 times per week. As the route of administration, intravenous or subcutaneous injection is used. The platelet production promoter of the present invention, furthermore, is used as a suppository or nasal drops.

The invention is further illustrated through the following examples.

BEST MODE FOR CARRYING OUT THE INVENTION

Example 1 Injection

The injection composed of the following compositions was prepared by the method described below.

10 mg of the chemically modified hG-CSF derivative obtained in Reference example 4 were dissolved into 80 ml of PBS solution, and added 2 mg of polysorbate 80 (Wako Pure Chemical Industries, Ltd.), 100 mg of human serum albumin (Sigma, Ltd.), and 1.5 g of D-mannitol, and adjusted to a volume of 100 ml with PBS. After aseptic filtration through a disposable membrane filter with a pore size of 0.22 µm, each 2 ml of the resulting solution was aseptically added to a glass vial to obtain the injection (containing 0.2 mg of active ingredients per vial).

| Prescription | |
|---|---|
| Chemically modified hG-CSF derivative (tri-type) | 0.2 mg |
| Polysorbate 80 | 0.04 mg |
| Human serum albumin | 2.0 mg |
| D-mannitol | 30 mg |
| NaCl | 16 mg |
| KCl | 0.4 mg |
| $KH_2PO_4$ | 0.4 mg |
| $Na_2HPO_4$ 12-hydrate | 5.8 mg |
| | 2.0 ml |

Example 2 Injection

The injection composed of the following compositions was prepared by the method described below.

50 mg of the chemically modified hG-CSF derivative obtained in Reference example 4 was dissolved into 80 ml of PBS solution, and added 2 mg of polysorbate 80 (Wako Pure Chemical Industries, Ltd.), and 1.5 g of D-mannitol, and adjusted to a volume of 100 ml with PBS. After aseptic filtration through a disposable membrane filter with a pore size of 0.22 µm, each 2 ml of the resulting solution was aseptically added to a glass vial to obtain the injection (containing 1.0 mg of active ingredients per vial).

| Prescription | |
|---|---|
| Chemically modified hG-CSF derivative (tri-type) | 1.0 mg |
| Polysorbate 80 | 0.04 mg |
| D-mannitol | 30 mg |
| NaCl | 16 mg |
| KCl | 0.4 mg |
| $KH_2PO_4$ | 0.4 mg |
| $Na_2HPO_4$ 12-hydrate | 5.8 mg |
| | 2.0 ml |

Example 3 Injection

The injection composed of the following compositions was prepared by the method described below.

10 mg of the chemically modified hG-CSF derivative obtained in Reference example 4 was dissolved into 80 ml of PBS solution, and added 2 mg of polysorbate 80 (Wako Pure Chemical Industries, Ltd.), 100 mg of human serum albumin (Sigma Ltd.), and 1.5 g of D-mannitol, and adjusted to about pH 5 with phosphoric acid and a volume of 100 ml with distilled water for injection. After aseptic filtration through a disposable membrane filter with a pore size of 0.22 µm, each 2 ml of the resulting solution was aseptically added to a glass vial to obtain the injection (containing 0.2 mg of active ingredients per vial).

| Prescription | |
|---|---|
| Chemically modified hG-CSF derivative (tri-type) | 0.2 mg |
| Polysorbate 80 | 0.04 mg |
| Human serum albumin | 2.0 mg |
| D-mannitol | 30 mg |

-continued

| Prescription | |
|---|---|
| NaCl | 12.8 mg |
| KCl | 0.32 mg |
| KH$_2$PO$_4$ | 0.32 mg |
| Na$_2$HPO$_4$ 12-hydrate | 4.64 mg |
| Phosphoric acid | q.s. |
| | 2.0 ml |

Example 4

35 ml of 50 mM phosphate buffer (pH 7.3) containing 31.5 mg of the hG-CSF derivative obtained in Reference example 3 were adjusted to pH 8.7 with 5% sodium hydroxide, and added 5.0 g of 2,4-bis (o-methoxypolyethylene glycol)-6-(1-aminopropyloxycarbonyloxy-4'-nitrophenyl)-s-triazine, and the reaction was performed at 4° C. for 7 days. To said reaction solution, ammonium sulfate was added at a final concentration of 0.7 M, and loaded onto a column (2.5 cm×6.1 cm=30 ml) of Butyl-Toyopearl 650M (Tosoh Corporation) equilibrated with 10 mM Tris-HCl buffer (pH 7.5) containing 0.7M ammonium sulfate at a flow rate of 30 ml/hr. After washing the column with 90 ml of 10 mM Tris-HCl buffer (pH 7.5) containing 0.7M ammonium sulfate at a flow rate of 30 ml/hr, the elution was performed with a decreasing linear gradient of ammonium sulfate concentration of from 0.7 to 0 M in 10 mM Tris-HCl buffer (pH 7.5) in a total volume of 180 ml at a flow rate of 30 ml/hr. The desired substance was eluted at ammonium sulfate concentrations of between 0.47 M and 0.16 M.

Ammonium sulfate was added at a final concentration of 0.7 M to the eluted fraction, and loaded onto a column (2.5 cm×12 cm=60 ml) of Butyl-Toyopearl 650M (Tosoh Corporation) equilibrated with 10 mM Tris-HCl buffer (pH 7.5) containing 0.7 M ammonium sulfate at a flow rate of 60 ml/hr. After washing the column with 180 ml of 10 mM Tris-HCl buffer (pH 7.5) containing 0.7 M ammonium sulfate at a flow rate of 60 ml/hr, the elution was performed with a decreasing linear gradient of ammonium sulfate concentration of from 0.7 to 0 M in 10 mM Tris-HCl buffer (pH 7.5) in a total volume of 600 ml at a flow rate of 60 ml/hr. The desired substance was eluted at ammonium sulfate concentrations of between 0.38 M and 0.11 M. 200 ml of the eluted fraction was ultrafiltrated [cutoff Mr or nominal molecular weight limit 10,000: YM10 (Amicon Co., Ltd.)] and concentrated to 6.5 ml. Said concentrated solution was loaded onto a column (2.5 cm×45 cm=220 ml) of Sephacryl S-300 (Pharmacia Co., Ltd.) equilibrated with PBS at a flow rate of 44 ml/hr, and then PBS was passed at the same flow rate.

After the initiation of PBS, the chemically modified hG-CSF derivative (tri-type) wherein 3 molecules of carboxylic acids of polyethylene glycol bound to one molecule of hG-CSF was eluted at between 92 ml and 100 ml, the chemically modified hG-CSF derivative (di-type) wherein 2 molecules of carboxylic acids of polyethylene glycol bound was eluted at between 100 ml and 104 ml, the chemically modified hG-CSF derivative (mono-type) wherein one molecule of carboxylic acids of polyethylene glycol bound was eluted at between 116 ml and 120 ml, with 1.0 mg (yield, 3.0%), 1.4 mg (Yield, 4.4%), and 1.1 mg (yield, 3.6%).

The number of molecules of polyethylene glycol derivatives binding to one molecule of the hG-CSF derivative in mono-type, di-type, and tri-type were confirmed by SDS-polyacrylamide gel electrophoresis.

Also, in the following reference examples, the number of molecules of binding polyethylene glycol derivatives and purity of the chemically modified hG-CSF derivative were confirmed by SDS-polyacrylamide gel electrophoresis.

Reference Example 1

Production of 6-chloro-2,4-bis(o-methoxypoly-ethylene glycol)-s-triazine 20 g of methoxypolyethylene glycol with a mean molecular weight of 4,000 (Nippon Oil and Fats Co., Ltd.) were dissolved into 100 ml of anhydrous toluene containing 10 g of anhydrous sodium carbonate, and heated at 110° C. for 30 minutes, and then added 500 mg of cyanuric chloride, and heated at 110° C. for 24 hours. The residual substances were removed, and 300 ml of petroleum ether were added for precipitation, and the said precipitates were washed several times with petroleum ether, and 10 g of the objective chloride were obtained (yield, 50%).

Reference Example 2

Production of N-hydroxysuccinimide ester of 6-(3-carboxybutylamino)-2,4-bis(o-methoxypolyethylene glycol)-s-triazine 500 mg of chlorides obtained in Reference example 1 was dissolved into 9 ml of anhydrous tetrahydrofuran. On the other hand, the above solution was added to a solution wherein 10 mg of gamma-amino butyric acid and 28 μl of triethylamine were dissolved into 1 ml of anhydrous N,N-dimethylformamide, and then stirred at room temperature for 16 hours. After exsiccation under reduced pressure, 30 ml of methylene chloride and 15 ml of 10 mM phosphate buffer (pH 10) for distribution. Their upper phase was adjusted to pH 1 with 2N hydrochloric acid, then 30 ml of methylene chloride were added, and the distribution was conducted again. The lower phase was fractionated, dried with anhydrous sodium sulfate, then filtered, concentrated under reduced pressure, and 150 mg of the objective carboxylic acid were obtained (yield, 30%).

150 mg of said carbonic acid and 3 mg of N-hydroxysuccinimide were dissolved into 1 ml of anhydrous methylene chloride, and after addition of 6 mg of N,N'-dicyclohexylcarbodiimide (DCC) on ice, was stirred at room temperature for 12 hours. The generating dicyclohexylurea (DCU) was filtered, exsiccated under reduced pressure, and 100 mg of the objective ester were obtained (yield, 67%).

Reference Example 3

The hG-CSF derivatives (Table 1, compound k), which comprise the amino acid sequence defined in SEQ ID NO:1 wherein the first amino acid, threonine was replaced by alanine, the third amino acid, leucine was replaced by threonine, the forth amino acid, glycine was replaced by tyrosine, the fifth amino acid, proline was replaced by arginine, and the seventeenth amino acid, cystine was replaced by serine respectively, was obtained as follows:

*E. coli* W3110 str A (*Escherichia coli* ECfBD28 FERM BP-1479) possessing plasmid pCfBD28 comprising DNA encoding said hG-CSF derivative was cultivated in LG medium [10 g of Bacto-tryptone, 5 g of yeast extract, 5 g of sodium chloride, and 1 g of glucose was dissolved into 1,000 ml of water, and adjusted to pH 7.0 with NaOH] at 37° C. for 18 hours, and 5 ml of the culture was inoculated into 100 ml of MCG medium (0.6% $Na_2HPO_4$, 0.3% $KH_2PO_4$, 0.5% sodium chloride, 0.5% casamino acids, 1 mM $MgSO_4$, 4 μg/ml vitamin $B_1$, pH 7.2) containing 50 μg/ml of ampicillin, at 30° C. for 4 to 8 hours, and then 10 μg/ml of 3 β-indole-acrylic acid (hereinafter referred to as IAA), a tryptophan derivative was added, further the cultivation was continued for 2 to 12 hours. The culture was centrifuged at 8,000 rpm for 10 minutes, the cells were collected, and washed with 30 mM sodium chloride and 30 mM Tris-HCl buffer (pH 7.5). The washed cells were suspended in 30 ml of said buffer, and ultrasonicated (BRANSON SONIC POWER COMPANY SONIFIER CELL DISRUPTOR 200, OUTPUT CONTROL 2) at 0° C. for 10 minutes. Said ultrasonicated debris was centrifuged at 9,000 rpm for 30 minutes to obtain pellets of the cells. From the pellet, according to the method of Marston et al. [F. A. O. Marston et al.: BIO/TECHNOLOGY, 2, 800 (1984)], the hG-CSF derivative was extracted purified, solubilized, and refolded.

Reference Example 4

To 100 ml of 50 mM phosphate buffer (pH 7.2) containing 300 mg of the hG-CSF derivative obtained in Reference example 3, 800 mg of the activated ester obtained in Reference example 2 were added, and the reaction was performed at 4° C. for 24 hours. After the addition of 100 ml of 10 mM Tris-HCl buffer (pH 8.0) containing 0.7 M ammonium sulfate, the reacted mixture was loaded onto a column (2.2 cm×26 cm) of Butyl-Toyopearl 650M (Tosoh Corporation) equilibrated with 10 mM Tris-HCl buffer (pH 8.0) containing 0.35 ammonium sulfate at a flow rate of 100 ml/hr. After washing the column with 100 ml of 10 mM Tris-HCl buffer (pH 8.0) containing 0.35 M ammonium sulfate at a flow rate of 100 ml/hr, elution was performed with a decreasing linear gradient of ammonium sulfate concentration from 0.35 to 0 M in 10 mM Tris-HCl buffer (pH 8.0) in a total volume of 400 ml at a flow rate of 100 ml/hr. The desired substance was eluted at ammonium sulfate concentrations between 0 mM and 250 mM. 250 ml of the eluted fraction was ultrafiltrated [Cutoff Mr or nominal molecular weight limit 10,000: YM10 (Amicon Co., Ltd.)] and concentrated to 10 ml. Said concentrated solution was loaded onto a column (5.6 cm×40 cm) of Sephacryl S-200 (Pharmacia Co., Ltd.) at a flow rate of 160 ml/hr, and then PBS was passed at the same flow rate.

After passing PBS, the chemically modified hG-CSF derivative (tri-type) wherein 3 molecules of carboxylic acids of polyethylene glycol bound to one molecule of hG-CSF was eluted at between about 360 ml and about 400 ml, the chemically modified hG-CSF derivative (di-type) wherein 2 molecules of carboxylic acids of polyethylene glycol bound was eluted at between about 420 ml and about 450 ml, the chemically modified hG-CSF derivative (mono-type) wherein one molecule of carboxylic acids of polyethylene glycol bound was eluted at between about 500 ml and about 530 ml, with 2.1 mg (yield: 7%), 1.5 mg (yield: 5%), and 1.5 mg (yield: 5%). The levels of purities of the mono-type, di-type, and tri-type are all more than 90%.

Reference Example 5

Production of N-hydroxysuccinimide ester of carboxyl methyl monomethoxypolyethylene glycol 4 g of sufficiently dehydrated carboxylmethyl monomethoxypolyethylene glycol (Nippon Oil and Fats Co., Ltd.) (0.8 mmol) with an average molecular weight of 5,000 and 184 mg of N-hydroxysuccinimide (HONSu) were dissolved into 40 ml of anhydrous methylene chloride, and added 300 mg of DCC on ice in a stream of argon, and stirred for 30 minutes. Subsequently, returning to room temperature, after stirring for 1.5 hours, an insoluble material (DCU) was filtered out, and the filtrate was concentrated to 16 ml under reduced pressure. The resulting solution was added dropwise to 240 ml of anhydrous diethyl ether to generate a precipitate, and after washing the precipitate with anhydrous diethyl ether, the solvent was removed under reduced pressure, and 2.8 g of the objective compound (0.56 mmol) was obtained (yield: 70%).

Reference Example 6

225 ml of 50 mM phosphate buffer (pH 7.3) containing 202.5 mg of the hG-CSF derivative obtained in Reference example 3 was adjusted to pH 8.1 with 5% sodium hydroxide, and 1.1 g of N-hydroxysuccinimide ester of carboxyl methyl monomethoxypolyethylene glycol obtained in Reference example 5 was added to said hG-CSF containing solution, and the reaction was performed at 4° C. for 6 hours. Subsequently, the reaction solution was obtained by adding 0.5 ml of an aqueous solution containing 26.7 mg of tris(hydroxymethyl)-amino methane. The reaction solution was centrifuged at 8,000 rpm, 4° C., for 40 minutes, and ammonium sulfate was added to 370 ml of the supernatant at a final concentration of 0.68 M, and the solution was loaded onto a column (5 cm×6.6 cm=130 ml) of Butyl-Toyopearl 650M (Tosoh Corporation) at a flow rate of 130 ml/hr.

After washing the column with 390 ml of 10 mM Tris-HCl buffer (pH 7.5) containing 0.68 M ammonium sulfate at a flow rate of 130 ml/hr, the elution was conducted with 390 ml of 10 mM Tris-HCl buffer (pH 7.5) at a flow rate of 130 ml/hr. The desired substance was eluted at between 35 ml and 80 ml. 45 ml of the eluted fraction were ultrafiltrated [cutoff Mr of nominal molecular weight limit 10,000: YM10] and concentrated to 30 ml. Said concentrated solution was loaded onto a column (5 cm×51 cm=1000 ml) of Sephacryl S-200 (Phamacia Co., Ltd.) equilibrated with PBS at a flow rate of 200 ml/hr, and then PBS was passed at the same flow rate. The chemically modified hG-CSF polypeptide was eluted at between about 200 ml and about 380 ml after passing PBS, which was a mixture of the combinations of 1 to 4 molecules of polyethylene glycol (mono-type to tetra-type) (total weight: 158 mg; yield: 78%).

Reference Example 7

Production of N-hydroxysuccinimide ester of carboxylmethyl monomethoxypolyethylene glycol 12 g of sufficiently dehydrated carboxylmethyl monomethoxypolyethylene glycol (Nippon Oil and Fats Co., Ltd.) (1.2 mmol) with an average molecular weight of 10,000 and 276 mg of HONSu were dissolved into 120 ml of anhydrous methylene chloride, and added 495 mg of DCC on ice in a stream of argon, and stirred for 30 minutes. Subsequently, returning to room temperature, after stirring for 1.5 hours, an insoluble material (DCU) was filtered out, and the filtrate was concentrated to 48 ml under reduced pressure. The resulting solution was added dropwise to 720 ml of anhydrous diethyl ether to generate a precipitate, and after washing the precipitate with anhydrous diethyl ether, the solvent was removed Reference Example 8

30 ml of 50 mM phosphate buffer (pH 7.3) containing 40.8 mg of hG-CSF comprising the amino acid sequence of SEQ ID NO:1 was adjusted to pH 8.3 with 5% sodium hydroxide, and added to 326 mg of N-hydroxysuccinimide ester of carboxyl methyl monomethoxypolyethylene glycol obtained in Reference example 7 on ice, and the reaction was conducted at 4° C. for 6 hours. Subsequently, the reaction solution was obtained by adding 0.1 ml of an aqueous solution of 3.9 mg of tris-(hydroxymethyl)amino methane. Ammonium sulfate was added to the reaction solution at a final concentration of 0.7 M, and loaded onto a column (2.5 cm×8.1 cm=40 ml) of Butyl-Toyopearl 650M (Tosoh Corporation) at a flow rate of 40 ml/hr.

After washing the column with 120 ml of 10 mM Tris-HCl buffer (pH 7.5) containing 0.7 M ammonium sulfate at a flow rate of 40 ml/hr, the elution was performed with a decreasing linear gradient of ammonium sulfate concentration of 0.7 to 0 M in 10 mM Tris-HCl buffer (pH 7.5) in a total volume of 240 ml at a flow rate of 40 ml/hr. The desired substance was eluted at ammonium sulfate concentration of between 0.33 M and 0.05 M. 90 ml of the eluted fraction was ultrafiltrated [cutoff Mr or nominal molecular weight limit 10,000: YM10 (Amicon Co., Ltd.)] and concentrated to 6 ml. Said concentrated solution was loaded onto a column (2.5 cm×45 cm=220 ml) of Sephacryl S-300 (Pharmacia Co., Ltd.) equilibrated with PBS at a flow rate of 44 ml/hr, and then PBS was passed at the same flow rate. The chemically modified hG-CSF polypeptide was eluted at between about 60 ml and about 102 ml after beginning PBS, which was a mixture of the combinations of 1 to 4 molecules of polyethylene glycol (mono-type to tetra-type) (total weight, 9.5 mg; yield, 23%).

Reference Example 9

338 ml of 50 M phosphate buffer (pH 7.3) containing 304.2 mg of the hG-CSF derivative obtained in Reference example 3 was adjusted to pH 8.1 with 5% sodium hydroxide, and 4.8 g of N-hydroxysuccinimide ester of carboxyl methyl monomethoxypolyethylene glycol obtained in Reference example 7 was added to said hG-CSF containing solution on ice, and the reaction was performed at 4° C. for 6 hours. Subsequently, the reaction solution was obtained by adding 0.5 ml of an aqueous solution containing 58.1 mg of tris (hydroxymethyl)amino methane. The reaction solution was centrifuged at 8,000 rpm, 4° C., for 40 minutes, and ammonium sulfate was added to the supernatant at a final concentration of 0.68 M, and the solution was loaded onto a column (5 cm×7.1 cm=140 ml) of Butyl-Toyopearl 650M (Tosoh Corporation) equilibrated with 10 mM Tris HCl buffer (pH 8.0) containing 0.68 M ammonium sulfate at a flow rate of 140 ml/hr.

After washing the column with 420 ml of 10 mM Tris-HCl buffer (pH 8.0) containing 0.68 M ammonium sulfate at a flow rate of 140 ml/hr, the elution was conducted with 420 ml of 10 mM Tris-HCl buffer (pH 8.0) at a flow rate of 140 ml/hr. The aimed substance was eluted at between 82 ml and 184 ml. The eluted fraction, 102 ml, was loaded onto a column (10 cm×50 cm=3,900 ml) of Sephacryl S-300 (Pharmacia Co., Ltd.) equilibrated with PBS at a flow rate of 780 ml/hr, and then PBS was passed at the same flow rate. The chemically modified hG-CSF polypeptide was eluted at between about 1,600 ml and about 2,070 ml after beginning PBS, which was a mixture of the combinations of 1 to 4 molecules of polyethylene glycol (mono-type to tetra-type) (total weight: 216 mg; yield: 71%).

Reference Example 10

Production of N-hydroxysuccinimide ester of 6-(3-carboxypropylamino)-2,4-bis(o-methoxypolyethylene glycol)-s-triazine 412 mg (4.0 mmol) of gamma-amino butyric acid was dissolved into 300 ml of 0.1 M borate buffer (pH 10), and 20 g (2 mmol) of 6-chloro-2,4-bis(o-methoxypolyethylene glycol)-s-triazine (SEIKAGAKU CORPORATION) was added on ice, and stirred at 4° C. overnight. After additionally stirring the mixture at room temperature for 6 hours, the solution was adjusted to pH 1 with 1 N hydrochloric acid, and extracted using chloroform. The chloroform phase was dried with anhydrous sodium sulfate, and separated by filtration after being dried. The solvent was removed under reduced pressure, and the generating solid was added to dried acetone, and dissolved. Said acetone solution was concentrated under reduced pressure, and the objective carboxylic acid was recrystallized by leaving it at room temperature, and 15.8 g (1.6 mmol) of said crystalline was obtained.

10 g (1.0 mmol) of said carboxylic acid and 230 mg of N-hydroxysuccinimide were dissolved into anhydrous methylene chloride, and added to 413 mg of DCC on ice in a stream of argon, and stirred for 30 minutes. Subsequently, after returning it to room temperature and stirring for 1.5 hours, an insoluble material (DCU) was filtered out, and the filtrate was concentrated to 40 ml under reduced pressure. The resulting solution was added dropwise into 600 ml of anhydrous diethyl ether to generate a precipitate, and after washing the precipitate with anhydrous diethyl ether, the solvent was removed under reduced pressure, and 7.7 g (0.77 mmol) of the objective compound was obtained (yield: 77%).

Reference Example 11

30 ml of 50 mM phosphate buffer (pH 7.3) containing 40.8 mg of hG-CSF comprising the amino acid sequence of SEQ ID NO:1 were adjusted to pH 7.2 with 5% sodium hydroxide, and 326 mg of N-hydroxysuccinimide ester of 6-(3-carboxypropyl-amino) -2,4-bis(o-methoxypolyethylene glycol)-s-triazine obtained in Reference example 10 was added on ice, and the reaction was conducted at 4° C. for 48 hours. Subsequently, the reaction solution was obtained by adding 0.1 ml of an aqueous solution of 3.9 mg of tris(hyrdoxymethyl) amino methane. Ammonium sulfate was added to the reaction solution at a final concentration of 0.7 M, and load onto a column (2.5 cm×8.1 cm=40 ml) of Butyl-Toyopearl 650M (Tosoh Corporation) at a flow rate of 40 ml/hr.

After washing the column with 120 ml of 10 mM Tris-HCl buffer (pH 7.5) containing 0.7 M ammonium sulfate at a flow rate of 40 ml/hr, the elution was conducted with a decreasing linear gradient of ammonium sulfate concentration of from 0.7 to 0 M in 10 mM Tris-HCl buffer (pH 7.5) in a total volume of 240 ml at a flow rate of 40 ml/hr. The desired substance was eluted at ammonium sulfate concentration between 0.35 M and 0.07 M. 90 ml of the eluted fraction was ultrafiltrated [cutoff Mr or nominal molecular weight limit 10,000: YM10 (Amicon Co., Ltd.)] and concentrated to 6 ml. Said concentrated solution was loaded onto a column (2.5 cm×47 cm=230 ml) of Sephacryl S-300 (Pharmacia Co., Ltd.) equilibrated with PBS at a flow rate of 46 ml/hr, and then PBS was passed at the same flow rate. The chemically modified hG-CSF polypeptide was eluted at between about 110 ml and about 145 ml after beginning PBS, which was a mixture of the combinations of 1 to 3 molecules of polyethylene glycol (mono-type to tri-type) (total weight, 7.8 mg; yield: 19%).

Reference Example 12

600 ml of 50 mM phosphate buffer (pH 7.3) containing 540 mg of the hG-CSF derivative obtained in Reference example 3 were adjusted to pH 7.2 with 5% sodium hydroxide, and 8.7 g of N-hydroxysuccinimide ester of 6-(3-carboxypropylamino)-2,4-bis(o-methoxypolyethylene glycol)-s-triazine obtained in Reference Example 10 was added on ice, and the reaction was conducted at 4° C. for 48 hours.

Subsequently, the reaction solution was obtained by adding 0.5 ml of an aqueous solution of 105 mg of tris-(hydroxymethyl)amino methane. The reaction solution was centrifuged at 8,000 rpm, 4° C., for 40 minutes, and ammonium sulfate was added to 600 ml of the supernatant at a final concentration of 0.68 M, and the solution was loaded onto a column (5 cm×18 cm=350 ml) of Butyl-Toyopearl 650M (Tosoh Corporation) equilibrated with 10 mM Tris-HCl buffer (pH 7.5) containing 0.68 M ammonium sulfate at a flow rate of 350 ml/hr.

After washing the column with 700 ml of 10 mM Tris-HCl buffer (pH 7.5) containing 0.68 M ammonium sulfate at a flow rate of 350 ml/hr, the elution was conducted with a decreasing linear gradient of ammonium sulfate concentration of from 0.68 to 0 M in 10 mM Tris-HCl buffer (pH 7.5) in a total volume of 2800 ml at a flow rate of 350 ml/hr. The desired substance was eluted at ammonium sulfate concentration of between 0.39 M and 0.20 M. 800 ml of the eluted fraction was ultrafiltrated [cutoff Mr 10,000: YM10 (Amicon Co., Ltd.)] and concentrated to 100 ml. Said concentrated solution was loaded onto a column (10 cm×50 cm=3900 ml) of Sephacryl S-300 (Pharmacia Co., Ltd.) equilibrated with PBS at a flow rate of 780 ml/hr, and then PBS was passed at the same flow rate. The chemically modified hG-CSF polypeptide was eluted at between about 1750 ml and about 2250 ml after beginning PBS, which was a mixture of the combinations of from 1 to 3 molecules of polyethylene glycol (mono-type to tri-type) (total weight: 303 mg; yield: 56%).

Reference Example 13

Production of 6-(3-carboxypropylamino)-2,4-bis(o-methoxypolyethylene glycol)-s-triazine 100 g (8.33 mmol) of sufficiently dehydrated monomethoxypolyethylene glycol (Nippon Oil and Fats Co., Ltd.) with an average molecular weight of 12,000, 9.3 g of zinc oxide (Wako Pure Chemical Industries, Ltd.), 83.5 g of molecular sieve (type 4A) (Wako Pure Chemical Industries, Ltd.) were dissolved in dried benzene, and left in a stream of argon overnight at room temperature. Subsequently, the molecular sieve was removed, and 42 g of molecular sieve were newly added, and the solution was left overnight, similarly. Next, the molecular sieve was removed, and the solution was distilled at 80° C. in a stream of argon using a distillator, and the first distillate, 50 ml, was removed. Further, using a Soxhlet extractor (for soil) loaded by 100 g of molecular sieve (type 4A), the solution was dehydrated with refluxing at 80° C. in a stream of argon overnight. After cooling, 36 mg (4.0 mmol) of cyanuric chloride was added to the reaction solution and similarly dehydrated with refluxing for 5 days. The cyanuric chloride recrystallized by dried diethyl ether was used in this case. Subsequently, the solution was cooled at room temperature, 300 ml of dried benzene was added to the solution, the solution was centrifuged at 3,600 rpm for 10 minutes, and insoluble materials were removed. The supernatant was concentrated under reduced pressure to 300 ml, and added dropwise to 3,000 ml of dried diethyl ether to generate a precipitate. Said precipitate was collected, and washed with dried diethyl ether, and then the solvent was removed under reduced pressure, and the dried precipitate was obtained.

100 g of said dried precipitate was added to 1,000 ml of 0.1 M borate buffer solution (pH 10), in which 24 g (12.0 mmol) of gamma-amino butyric acid were dissolved in 1,000 ml of the buffer, on ice, and stirred at 4° C. overnight. After additionally stirring at room temperature for 6 hours, the solution was adjusted to pH 1.0 with 1N hydrochloric acid, and extracted with chloroform. The chloroform phase was dried with anhydrous sodium sulfate, and separated by filtration, and the solvent was removed under reduced pressure. Dried acetone was added to the generating white solid and the solid was dissolved. Said acetone solution was concentrated under reduced pressure, and made to recrystallize by leaving it at room temperature, and 90 g of the rough product containing about 70 to 80% of the target compound was obtained. This product was dissolved into 6,000 ml of distilled water, and loaded onto a column of anion exchange resin HPA-75 (Mitsubishi Chemical Corporation), which was equilibrated with distilled water after previously passing 12,000 ml of 2N sodium hydride, and the fractions containing the subject compound as a main ingredient were collected by eluting with distilled water. The resulting solution was adjusted to pH 1.0 with 1N hydrochloric acid, and extracted with chloroform. The chloroform phase was dried with anhydrous sodium sulfate and separated by filtration, and the solvent was removed under reduced pressure, and 43.6 g of the highly purified objective compound were obtained (yield: 43%).

Reference Example 14

Production of N-hydroxysuccinimide ester of 6-(3-carboxypropylamino)-2,4-bis(o-methoxypolyethylene glycol)-s-triazine 25 g of 6-(3-carboxypropylamino)-2,4-bis(o-methoxypolyethylene glycol)-s-triazine which was synthesized and sufficiently dried according to the method of Reference example 13 and 240 mg of N-hydroxysuccinimide were dissolved into 400 ml of anhydrous methylene chloride, and added to 431 mg of DCC on ice in a stream of argon, and stirred for 30 minutes. Subsequently, after returning to room temperature and stirring for 1.5 hours, an insoluble material (DCU) was filtered out, and the filtrate was concentrated under reduced pressure to 160 ml. The resulting solution was added dropwise to 2,400 ml of anhydrous diethyl ether to generate a precipitate, and after washing said precipitate with anhydrous diethyl ether, the solvent was removed under reduced pressure, and 21.4 g (0.89 mmol) of the target compound was obtained (yield, 89%).

Reference Example 15

560 ml of 50 mM phosphate buffer (pH 7.3) containing 504 mg of the hG-CSF derivative obtained in Reference example 3 were adjusted to pH 7.3 with 5% sodium hydroxide, and 22.4 g of N-hydroxysuccinimide ester of 6-(3-carboxypropylamino)-2,4-bis(o-methoxypolyethylene glycol)-s-triazine obtained in Reference example 14 was added on ice, and the reaction was conducted at 4° C. for 48 hours. Subsequently, the reaction solution was obtained by adding 0.5 ml of an aqueous solution of 113 mg of tris (hydroxymethyl)-amino methane. Ammonium sulfate was added at a final concentration of 0.7 M to the reaction solution, and the solution was loaded onto a column (5 cm×25 cm=500 ml) of Butyl-Toyopearl 650M (Tosoh Corporation) equilibrated with 10 mM Tris-HCl buffer (pH 7.5) containing 0.7 M ammonium sulfate at a flow rate of 500 ml/hr. After washing the column with 1,500 ml of 10 mM Tris-HCl buffer (pH 7.5) containing 0.7M ammonium sulfate at a flow rate of 500 ml/hr, the elution was conducted with a decreasing linear gradient of ammonium sulfate concentration from 0.7 to 0 M in 10 mM Tris-HCl buffer (pH 7.5) in a total volume of 3,000 ml at a flow rate of 500 ml/hr. The desired substance was eluted at ammonium sulfate concentration of between 0.55 and 0.08 M. Ammonium sulfate was added to the eluted fraction at a final concentration of 0.7 M, and loaded onto a column (5 cm×15 cm=300 ml) of Butyl-Toyopearl 650M (Tosoh Corporation) equilibrated with 10 mM Tris-HCl buffer (pH 7.5) containing 0.7 M ammonium sulfate at a flow rate of 450 ml/hr. After washing the column with 1,500 ml of 10 mM Tris-HCl buffer (pH 7.5) containing 0.7 M ammonium sulfate at a flow rate of 450 ml/hr, the elution was conducted with 900 ml of 10 mM Tris-HCl buffer (pH 7.5) at a flow rate of 450 ml/hr. The desired substance was eluted to between 67 ml and 132 ml. The eluted fraction, 100 ml, was loaded onto a column (5 cm×50 cm=1000 ml) of Sephadex G-25 (Pharmacia Co., Ltd.) equilibrated with PBS at a flow rate of 300 ml/hr. Subsequently, PBS was passed by at the same flow rate. The chemically modified hG-CSF polypeptide was eluted at between about 350 ml and about 500 ml after beginning PBS, which was a mixture of the combinations of 1 to 4 molecules of polyethylene glycol (mono-type to tetra-type) (total weight: 282 mg; yield: 56%).

Reference Example 16

Production of 4-nitrophenyloxycarbonyl (o-methoxypolyethylene glycol)

5.5 g of sufficiently dehydrated methoxypoly-ethylene glycol (Nippon Oil and Fats Co., Ltd.) (0.55 mmol) with an average molecular weight of 10,000 were dissolved into 27.5 ml of dried methylene chloride, and 0.153 ml of triethylamine and 222 mg of 4-nitrophenyl chloroformate were added and stirred in a stream of argon at room temperature for 4 hours. During stirring, the pH was kept at between 7.5 and 8.5 by adding triethylamine. The reaction solution was concentrated to 20 ml under reduced pressure, and added dropwise to 300 ml of dried diethyl ether to generate a precipitate. Said precipitate was recrystallized with ethyl acetate, and 4.8 g of the target compound was obtained by drying under reduced pressure (0.48 mmol) (yield, 87%).

Reference Example 17

45 ml of 50 mM phosphate buffer (pH 7.3) containing 40.5 mg of the hG-CSF derivative obtained in Reference example 3 was adjusted to pH 8.7 with 5% sodium hydroxide, and 4.3 g of 4-nitrophenyloxycarbonyl (o-methoxypolyethylene glycol) obtained in Reference Example 16 was added on ice, and the reaction solution was obtained by reacting them at 4° C. for 3 days. Ammonium sulfate was added to the reaction solution at a final concentration of 0.7M, and loaded onto a column (2.5 cm×12 cm=60 ml) of Butyl-Toyopearl 650M (Tosoh Corporation) equilibrated with 10 mM Tris-HCl buffer (pH 7.5) containing 0.7 ammonium sulfate at a flow rate of 60 ml/hr. After washing the column with 180 ml of 10 mM Tris-HCl buffer (pH 7.5) containing 0.7 M ammonium sulfate at a flow rate of 60 m/hr, an elution was performed with a decreasing linear gradient of ammonium sulfate concentration from 0.7 to 0 M in 10 mM Tris-HCl buffer (pH 7.5) in a total volume of 360 ml at a flow rate of 60 ml/hr.

Subsequently, the remaining uneluted portion was eluted by passing 180 ml of 10 mM Tris-HCl buffer (pH 7.5). The desired substance was eluted at ammonium sulfate concentrations from 0.4 M to 0 M. The eluted fraction, 210 ml, was ultrafiltrated [cutoff Mr 10,000: YM10 (Amicon Co., Ltd.)] and concentrated to 30 ml. Said concentrated solution was loaded onto a column (5 cm×51 cm=1000 ml) of Sephacryl S-300 (Pharmacia Co., Ltd.) equilibrated with PBS at a flow rate of 200 ml/hr, and then PBS was passed by at the same flow rate.

After beginning PBS, the chemically modified hG-CSF derivative (tri-type) wherein 3 molecules of carboxylic acids of polyethylene glycol bound to one molecule of hG-CSF was eluted at between about 285 ml and about 305 ml, the chemically modified hG-CSF derivative (di-type) wherein 2 molecules of carboxylic acids of polyethylene glycol bound was eluted at between about 325 ml and about 345 ml, the chemically modified hG-CSF derivative (mono-type) wherein one molecule of carboxylic acids of polyethylene glycol bound was eluted at between about 365 ml and about 385 ml, with 6.2 mg (yield: 10.9%), 6.8 mg (yield: 11.9%), and 5.0 mg (yield: 8.8%).

Reference Example 18

Production of 6-(1-aminopropyloxycarbonyloxy-4'-nitrophenyl)-2,4-bis(o-methoxypolyethylene glycol)-s-triazine 120 mg (1.6 mmol) of 3-amino-1-propanol was dissolved into 200 ml of 0.1 M borate buffer (pH 10), and 8 g (0.8 mmol) of 6-chlor-2,4-bis(o-methoxypolyethylene glycol)-s-triazine (SEIKAGAKU CORPORATION) was added on ice, and stirred at 4° C. overnight. The reaction solution was adjusted to pH 1.0 with 2 N hydrochloric acid, and extracted with chloroform. After washing twice with 2 N hydrochloric acid, the chloroform phase was dried with anhydrous sodium sulfate, and filtered. The solvent was removed under reduced pressure, and dried acetone was added to the generating solid, and the solid was dissolved. Said acetone solution was concentrated under reduced pressure, and polyethylene glycol derivative was recrystallized by leaving it at room temperature, and 5.5 g of said crystalline substance was obtained (yield: 69%).

Subsequently, 5.3 g (0.53 mmol) of said polyethylene glycol derivative sufficiently dried was dissolved into 26.5 ml of dried methylene chloride, 0.147 ml of triethylamine was added, and further 214 mg (1.06 mmol) of 4-nitrophenyl chloroformate was added, and stirred at 4° C. for 4 hours. Subsequently, the reaction solution was concentrated to 20 ml under reduced pressure, and added dropwise to 300 ml of dried diethyl ether to generate a precipitate. The precipitate was washed with dried diethyl ether, and after removing the solvent under reduced pressure, recrystallized by dried ethyl acetate, and 4.6 g (0.46 mmol) of the objective compound was obtained by drying it under reduced pressure (yield, 87%).

Reference Example 19

287 mg of activated polyethylene glycol M-SCM-20,000 (Shearwater Polymer, Inc.) was added to 6.5 ml of 50 mM phosphate buffer (pH 7.5) containing 29.25 mg of the hG-CSF derivative obtained in Reference example 3, and the reaction was performed at 4° C. for 6 hours, and then the reaction solution was obtained by adding 35 μl of 50 mg/ml tris(hydroxymethyl)amino methane. Said reaction solution was loaded onto a column (2.5 cm×45 cm=220 ml) of Sephacryl S-300 (Pharmacia Co., Ltd.) equilibrated with PBS at a flow rate of 44 ml/hr, and then PBS was passed by at the same flow rate.

After beginning PBS, the chemically modified hG-CSF polypeptide (di-type), wherein 2 molecules of carboxylic acids of polyethylene glycol bound, was eluted at between about 96 ml and about 104 ml, and 3.8 mg of said di-type was obtained (yield: 13.0%).

Reference Example 20

98 mg of activated polyethylene glycol M-SSPA-20,000 (Shearwater Polymer Inc.) was added to 6.7 ml of 50 mM phosphate buffer (pH 7.5) containing 28.8 mg of the hG-CSF derivative obtained in Reference example 3, and the reaction was performed at 4° C. for 24 hours, and then the reaction solution was obtained by adding 30 μl of 40 mg/ml tris-(hydroxymethyl)amino methane. Said reaction solution was loaded onto a column (2.5 cm×45 cm=220 ml) of Sephacryl S-300 (Pharmacia Co., Ltd.) equilibrated with PBS at a flow rate of 44 ml/hr, and then PBS was passed by at the same flow rate.

After beginning PBS, the chemically modified hG-CSF polypeptide (tri-type) wherein 3 molecules of carboxylic acids of polyethylene glycol bound, was eluted at between about 78 ml and about 98 ml, and 2.0 mg of said tri-type was obtained (yield: 6.6%).

INDUSTRIAL UTILIZATION

The present invention can provide a chemically modified polypeptide, wherein at least one group of amino, carboxyl, mercapto and guanidino groups in a polypeptide molecule having hG-CSF is modified chemically, and an excellent platelet production promoting agent comprising said modified polypeptide.

We claim:

1. A method for increasing the platelet counts of a patient with decreased platelet counts comprising administering an effective amount of a modified polypeptide having an amino acid sequence wherein the first amino acid, threonine is replaced by alanine, the third amino acid, leucine is replaced by threonine, the fourth amino acid, glycine is replaced by tyrosine, the fifth amino acid, proline is replaced by arginine and the seventeenth amino acid, cysteine is replaced by serine, respectively in SEQ ID NO: 1, wherein at least one group of the amino, carboxyl, mercapto or guanidino group in the molecule of a polypeptide is chemically modified with a polyalkylene glycol derivative or a stylene-maleic acid copolymer.

2. The method according to claim 1, wherein a polyalkylene glycol derivative is selected from the group consisting of a polyethylene glycol derivative, a polypropylene glycol derivative, and a derivative of polyethylene glycol-polypropylene glycol copolymer.

3. The method according to claim 1, wherein the amino group is modified with (a) a polyalkylene glycol derivative having the formula (I):

$$R^1\text{-}(M)_n\text{—}X\text{—}R^2 \quad (I)$$

wherein $R^1$ represents alkyl or alkanoyl group; M represents the formula:

—OCH$_2$CH$_2$—, —OCH$_2$CH$_2$CH$_2$— or

—(OCH$_2$CH$_2$)$_r$—(OCH$_2$CH$_2$CH$_2$)$_s$— wherein r and s have any variable positive integral values, which are the same or different; n has any variable positive integral values; X represents a single bond, O, NH, or S; and $R^2$ represents the formula:

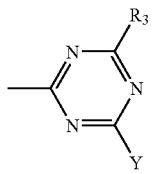

wherein $R^3$ represents OH, halogen, or the formula:

$$X^a\text{-}(M^a)_{na}\text{-}R^{1a}$$

wherein $X^a$, $M^a$, $R^{1a}$ and na are identical to said X, M, $R^1$ and n, respectively, and Y represents halogen or the formula:

$$\text{-}Z\text{-}(CH_2)_p\text{—}(O)_m\text{—}W$$

wherein Z represents O, S, or NH; W represents a carboxyl group, an active derivative thereof, or the formula:

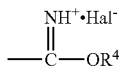

wherein $R^4$ represents an alkyl group; and Hal represents halogen, and p has an integral value of 1 to 6; and m has a value of 0 or 1, —(CO)$_{ma}$—(CH$_2$)$_t$—W$^a$ wherein $W^a$ and ma are identical to said W and m, respectively; and t has an integral value of from 0 to 6, or

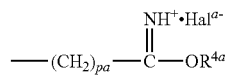

wherein Hal$^a$, pa and $R^{4a}$ are identical to said Hal, p and $R^4$, respectively, or (b) a styrene-maleic acid copolymer having the formula (II):

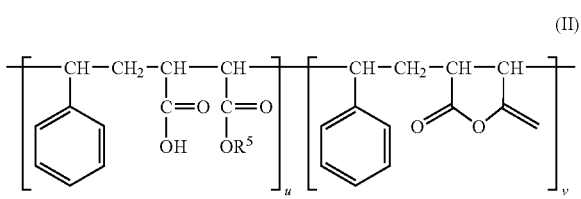

wherein u and v have any variable positive integral values, which are the same or different; and $R^5$ represents a hydrogen atom, or an alkyl group.

4. The method according to claim 1, wherein the carboxyl group is modified with a polyalkylene glycol derivative having the formula (III):

$$R^{1b}\text{-}(M^b)_{nb}\text{-}NH_2 \quad (III)$$

wherein $M^b$, $R^{1b}$ and nb are identical to said M, $R^1$ and n, respectively.

5. The method according to claim 1, wherein the mercapto group is modified with (a) a polyalkylene glycol derivative having the formula (IV):

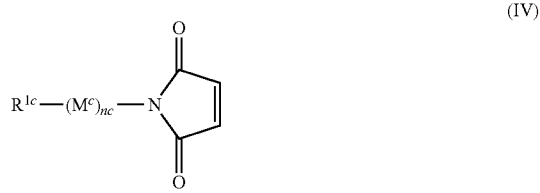

wherein $M^c$, $R^{1c}$, and nc are identical to said M, $R^1$, and n, respectively, or (b) a styrene-maleic acid copolymers having the formula (V):

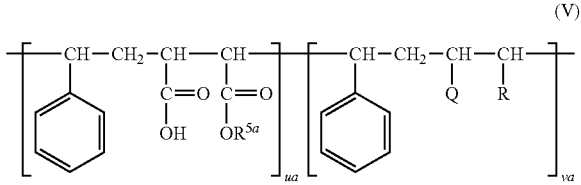

wherein $R^{5a}$, ua, and va are identical to said $R^5$, U and V, respectively, and one of Q and R represents a carboxyl group, and the other represents the formula:

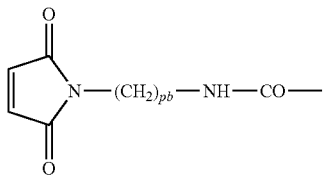

herein pb is identical to said p.

6. The method according to claim 1, wherein the guanidino group is modified with a polyalkylene glycol derivatives having the formula (VI):

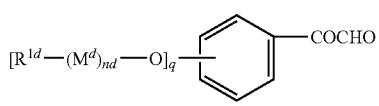
(VI)

wherein q has a value of 1 or 2, and $M^d$, $R^{1d}$, and nd are identical to said M, R1, and n, respectively.

7. The method according to claim 1, wherein the amino group is modified by binding to a group represented by the following formula (Ia):

$$R^1\text{-}(M)_n\text{-}X\text{—}R^{2a}\text{—}\qquad(Ia)$$

wherein $R^1$ represents an alkyl or alkanoyl group; M represents the formula:

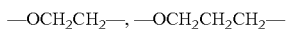

or

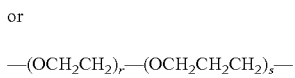

wherein r and s have any variable positive integral values, which are the same or different; n has any variable positive integral value; X represents a single bond, O, NH, or S; and $R^{2a}$ represents the formula:

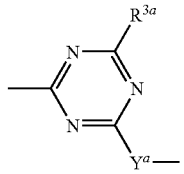

wherein $R^{3a}$ represents OH, halogen, or the formula:

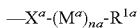

wherein $X^a$, $M^a$, $R^{1a}$ and na are identical to said X, M, $R^1$ and n, respectively, and $Y^a$ represents a single bond, the formula:

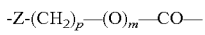

wherein Z represents O, S, or NH; p has an integral value of from 1 to 6; and m has a value of 0 or 1, or the formula:

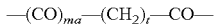

wherein ma is identical to said m; and t has an integral value of from 0 to 6.

8. The method according to claim 7, wherein $Y^a$ represents the formula:

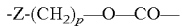

wherein Z represents O, S, or NH; and p has an integral value of from 1 to 6.

* * * * *